US005297553A

United States Patent [19]

Sliwa, Jr. et al.

[11] Patent Number: 5,297,553

[45] Date of Patent: Mar. 29, 1994

[54] ULTRASOUND TRANSDUCER WITH IMPROVED RIGID BACKING

[75] Inventors: John W. Sliwa, Jr., Palo Alto; Sevig Ayter, Cupertino; Champa G. Sridhar, Los Altos; John P. Mohr, III, San Jose; Samuel M. Howard, Mountain View; Michael H. Ikeda, San Jose, all of Calif.

[73] Assignee: Acuson Corporation, Mountain View, Calif.

[21] Appl. No.: 949,719

[22] Filed: Sep. 23, 1992

[51] Int. Cl.[5] ............................................. A61B 8/00

[52] U.S. Cl. ............................ 128/662.03; 310/334; 29/25.35

[58] Field of Search ..................... 128/662.03–662.06; 73/633; 310/334; 29/25.35

[56] References Cited

U.S. PATENT DOCUMENTS

| | | | |
|---|---|---|---|
| 4,086,916 | 5/1978 | Freeman et al. | 128/690 X |
| 4,769,793 | 9/1988 | Kniest et al. | 367/99 |
| 4,917,097 | 4/1990 | Proudian | 128/662.06 |

*Primary Examiner*—Francis Jaworski

[57] ABSTRACT

An ultrasound transducer comprising an array of individual piezoelectric transducer elements mounted upon an improved backing comprising rigid polymeric or polymer-coated particles fused into a macroscopically rigid structure having remnant tortuous permeability to provide high acoustic attenuation and to permit fluid passage into the backing structure during fabrication.

18 Claims, 1 Drawing Sheet

ULTRASOUND TRANSDUCER WITH IMPROVED RIGID BACKING

BACKGROUND OF THE INVENTION

There is a substantial interest in miniaturizing medical imaging ultrasound transducers so that they can be inserted into various body openings to gain better access to body parts for ultrasound imaging purposes. An example is one or more transducer arrays mounted on a gastroscope for insertion down a patient's throat so that the heart can be imaged from the esophagus. Transesophageal probes having one 64-element transducer array as well as a pair of transducer arrays arranged orthogonally have been employed to obtain duplex orthogonal ultrasound images of the heart.

SUMMARY OF THE INVENTION

This invention comprises an ultrasound transducer having one or more arrays of piezoelectric transducer elements separated by kerfs and a top and bottom electrode for individually addressing each element all mounted upon an improved backing which comprises rigid polymeric or polymer-coated particles fused into a macroscopically rigid structure having remnant tortuous permeability to provide high acoustic attenuation and to permit fluid passage into the backing structure.

One object of the invention is to provide a rigid backing structure useful for miniaturizing transducer arrays without compromising image performance and at the same time enabling reliability and ease of manufacture.

Another object of the invention is to provide a compact backing of fused particles that is very light in weight, has high acoustic attenuation, minimal acoustic backscattering, low acoustic impedance, substantial structural integrity, thermal stability, permeability which permits vacuum evacuation and backfilling and superior adhesion because of its high surface roughness.

A further object of the invention is to provide a fused particle backing that has sufficient elasticity to be bent across a gentle radius for shaping curvilinear arrays.

One further object of the invention is to provide a backing that has a high transition temperature to enable ease of dicing and other manufacturing procedures.

These and other advantages of the invention will become apparent upon consideration of the following detailed description and the accompanying drawings.

BRIEF DESCRIPTION OF A PREFERRED EMBODIMENT

Figure 1:
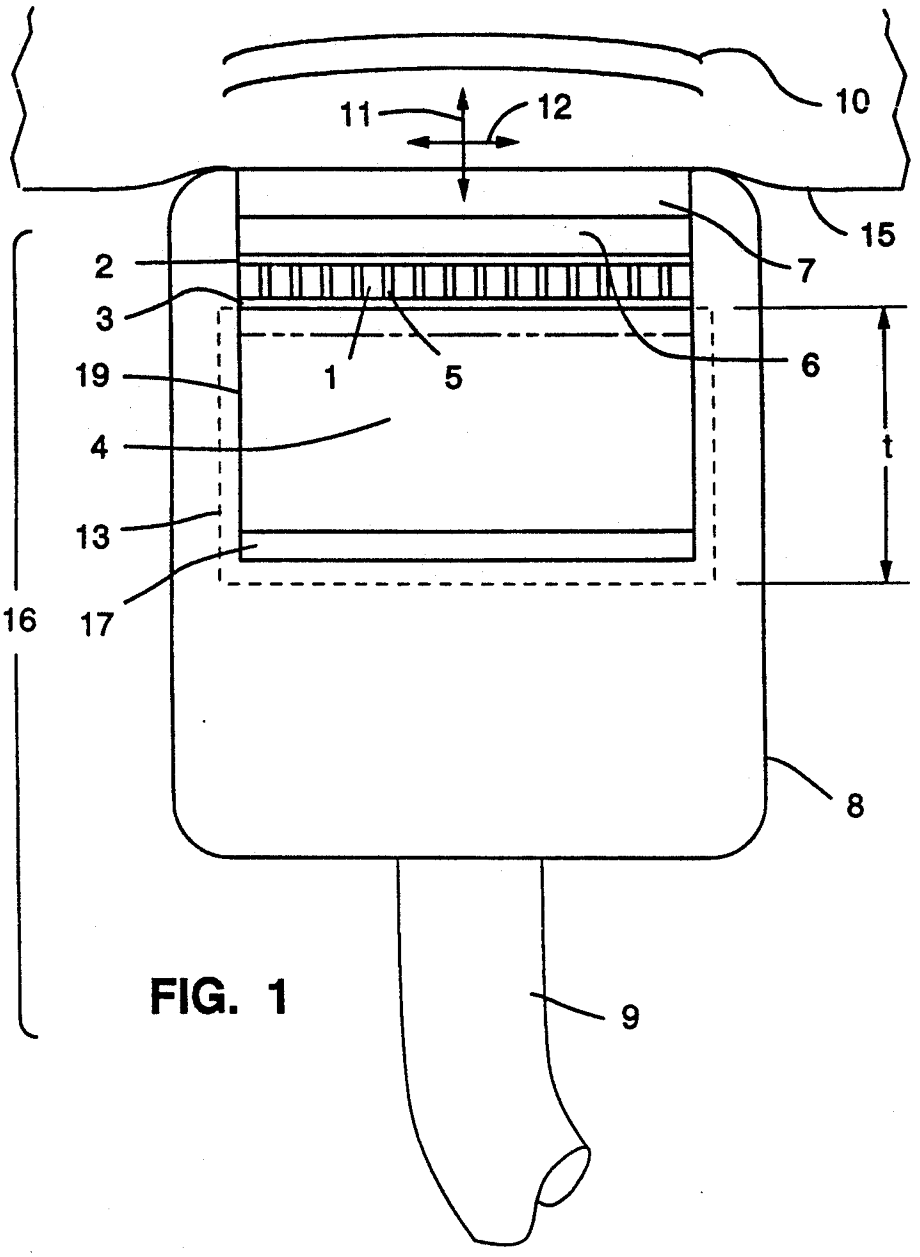
FIG. 1 is a view partly in section of a typical medical imaging transducer.

FIG. 1 illustrates the principal components of a medical imaging transducer 16 deployed against a patient's skin-line 15. The transducer is shown in section through its azimuth plane with the azimuth direction 12 in the plane of the drawing. A single array of piezoelectric elements 1, shown in section, runs into and out of the drawing in the transducer elevation direction. Transmit and receive acoustic beams are formed in the azimuth plane by time-gating the switching of each piezoelectric element 1 in a phased array format. There may be typically 64 to 128 electrically-independent piezoelectric elements 1 in the array. A top electrode 2 overlying and a bottom electrode 3 underlying each piezoelectric element enables each element 1 to be individually electrically addressed. One electrode may be a common electrical connection such as ground. Acoustic backing 4 provides structural support for the array of transducer elements 1 and their associated electrodes 2 and 3.

Gaps or kerfs 5 cut between individual piezoelectric elements 1 achieve acoustic isolation between them. An acoustic matching layer 6 typically provides acoustic impedance transition between the transducer elements 1 and the acoustic lens and patient's body tissue. The overlying acoustic focussing lens 7 typically achieves acoustic focussing in the elevation plane perpendicular to the drawing. An external case 8, which the operator grasps during use, encloses the transducer assembly. Cable 9 electrically connects the transducer to the imaging system electronics and typically has one wire per acoustic transducer element 1 in addition to grounds and other service wires.

Ultrasound waves 10 are transmitted into the patient either normal to the face of the transducer array as shown or at an angle as necessary to sweep the field of view for the image format in use. Arrows 11 and 12, respectively, indicate directions in which normal and shear-stresses are imposed upon the face of the transducer as it is scanned and otherwise manipulated against the patient's skin 15 by the operator for purposes of varying the field of view or skin contact force. An optional container 13 can be provided for additional physical integrity to backing 4 as well as for thermal and electromagnetic benefits. An optional bonding adhesive layer 17 also can be added to mechanically attach backing 4 to the container 13.

The attenuative backing 4, to which the piezoelectric elements 1 and their associated electrodes 2,3 matching layer 6 and focussing lens 7 are joined, is particularly challenging to downsize. This is because the depth or thickness "t" of that backing is dictated by the acoustic requirement of attenuating reflected acoustic waves from its back surface to a negligible level compared to the reflected acoustic signal coming from the patient. This demands a very attenuative material. Backing 4 also generally provides mechanical rigidity to the assembly and must have a specific acoustic impedance compatible with the acoustic design.

Materials heretofore used for backing include rubber and/or epoxy matrices with dispersed solid metallic or ceramic filler particles of a chosen density. They lack the needed high acoustic attenuation or the needed mechanical rigidity in thicknesses of a millimeter to a few millimeters necessary for miniaturization and ease of manufacture. Other rubbery or gellike materials have been conveniently cast or molded directly to the transducer assembly. Although these can attenuate better in minimal thicknesses, they have little structural integrity and, therefore, serve as poor foundations on which to fabricate a multielement transducer array simply because it becomes extremely difficult to maintain planarity of the piezoelectric elements 1. Transducer array non-flatness causes acoustic phase errors which degrade image quality.

A second drawback of such "soft" backing materials is that, when the transducer is in use, the array is subjected to mechanical loads in the directions 11 and 12. Physical distortion of or damage to the elements in the array results in resolution loss and reduction of image quality. A third disadvantage of soft backing materials is that to avoid distortion one must provide an alternative means of maintaining array rigidity (flatness) during fabrication and transducer use. Those alternative means may have significant acoustic and/or fabrication penalties associated with them.

Figure 2:
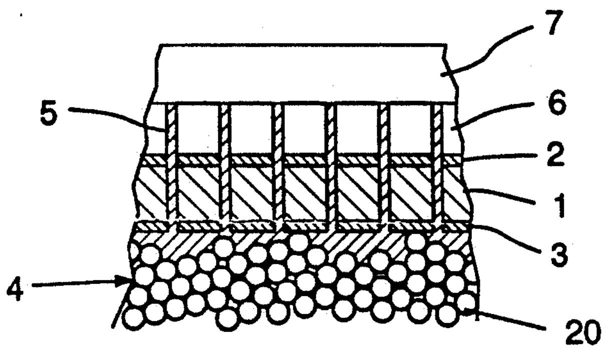
FIG. 2 is a cross-sectional view of a portion of the transducer array and related elements illustrating the improved backing structure of fused polymeric particles according to this invention.

The matching layer 6 is typically diced with kerfs 5 in the same manner as are the piezoelectric elements 1 as is shown in the enlarged detail of FIG. 2. This dramatically reduces the acoustic crosstalk between elements 1. FIG. 1 shows a continuous matching layer 6, as it would have to be if one were to rely upon it rather than backing 4 as a substrate on which to build the array of piezoelectric elements 1 and to rigidify them during use of the transducer. However, the matching layer is typically too thin to provide any meaningful flexural or shear rigidity even in the undiced form of FIG. 1. Thus, the matching layer of FIG. 1, although providing modest structural rigidity, would invite far worse element acoustic crosstalk than if it were diced as shown in FIG. 2.

The permeable backing materials of this invention consist of materials made by fusing together rigid polymeric or polymeric-coated particles in a manner such that the fusing process leaves a remnant tortuous permeability which results in very high acoustic attenuation and scattering and permits ingress of acoustically lossy solidifying liquid filler materials but still provides for macroscopic rigidity. Such polymer particles or particle coatings do not include cast rubbers, elastomers or gels as are widely used in prior art transducers.

In a first embodiment shown in FIG. 2, solid or thick-walled (OD/ID 3:1) hollow particles 20 are polymeric in composition and have a generally spherical, rodlike or platelike shape. They are joined together by direct-bonding processes such as thermoplastic welding, thermoforming, acoustic welding, solvent welding or thermal diffusion-bonding or alternatively by indirect bonding processes such as by the gaseous intrusion coating and impregnation of compacted particles with continuous vapor deposition of polymer such as parylene polymer. There are a number of parylenes available to do this including parylene N, parylene C, parylene D and parylene E.

The vapor deposition process is particularly useful because it is capable of coating a very thin and tough organic coating onto everything the polymer vapor contacts or saturates in a deposition chamber. An example is the Union Carbide CVD conformal PARYLENE process described in U.S. Pat. No. 3,342,754 entitled "Para-xylylene Polymers" issued Sep. 19, 1967. That process can saturate a sugar cube. The sugar can then be dissolved leaving behind a cube of porous PARYLENE which is an exact replica of the sugar cube's original pore structure. Mechanical rigidity is achieved by using PARYLENE for the fusing of the compacted polymer particles which, themselves, contact each other and remain in the structure. Parylenes have useful glass transition temperatures ($T_{gs}$) in the range of 60°-100° C.

Specific examples of powdered or granulated materials suited for fusing to form backing 4 for this acoustic application include plastics having glass-transition temperatures in the general range of 100° C. or above selected from the group consisting of polysulfone (PS), polyethersulfone (PES), polycarbonate (PC), polytetrafluoroethylene (PTFE), polyvinylidene fluoride (PVDF), ultrahigh density high molecular weight polyethylene (UDHMWPE), low and medium density polyethylene (PE), perfluoroalkoxy (PFA), fluorinated ethylene propylene (FEP), polytrifluorochloroethylene (CTFE), chlorotrifluoroethylene (CTFE, ECTFE), polyaryl sulfone, polyester and acrylonitrilebutadiene-styrene (ABS).

Highly acoustically attenuative and rigid backings can be made using the above materials. The resultant backings are thin, on the order of three millimeters thick, and are fluid permeable.

Such fused backing materials have a resulting median pore size in the range of 15-100 microns and most preferably in the range of 35-55 microns and a glass transition temperature above 100° C. and preferably closer to 200° C. Particles with the higher glass transition temperatures simply provide more thermal stability, less creep and typically more rigidity. Pores larger than that specified begin to cause problems such as acoustic backscattering, especially for higher-frequency transducers and the lack of local mechanical support for individual piezoelectric elements in the region of a pore. Pores smaller than that reduce attenuation and make impregnation difficult.

Fused backing materials meeting the above description offer the rare combination of very light weight, very high acoustic attenuation of at least 3 dB/mm and as much as 8 dB/mm (at 1 Mhz), minimal acoustic backscattering, low acoustic impedance, substantial structural integrity, substantial thermal stability, permeability (which allows vacuum evacuation and backfilling and/or potting of the kerfs and backing) for superior adhesion of kerf-filling materials and adjacent layers such as electrode 3 due to the high surface roughness of backing material 4. These fused materials may also be bent across a gentle radius elastically for a curvilinear probe application. Finally these backing materials, having a glass transition temperature approaching 200° C. in some cases, are easy to dice during the element patterning operation without unacceptable blade loading due to abrasive melting of backing material 4.

The backings of this implementation of the invention are thermally stable, of light weight, are rigid and have low acoustic impedance. They can be very thin to allow for even smaller and lighter transducers but at the same time can permit building-up of the transducer upon backing 4 as a convenient and stable fabrication foundation. They have a substantial in-use stiffening function. They also provide for wide thermal latitude in transducer fabrication processing and minimal injection of acoustic energy. They are elastically formable over a gentle radius such that the piezoelectric element array can be arranged on a curved surface as for a curvilinear probe (not shown) after it is first fabricated in a flat configuration.

These fused backings are permeable and allow the kerfs 5 to be optionally filled with an acoustically attenuative organic filler material such as eccogel or an RTV silicone after piezoelectric elements 1, electrodes 2 and 3 and backing 4 are preassembled. Such filling can be via passage of the kerf-filling material through the permeable bulk of backing 4. Impregnating filler material can serve chemical passivation (potting), mechanical reinforcement/array stiffening, thermal heatsinking and electrical breakdown improvement functions as well as outgassing/venting reduction functions. The ability to introduce kerf-fillers after critical transducer laminations are totally completed is important because the best kerf-filling materials are typically difficult to clean up and frequently also have poor thermal stability. Such materials can interfere with the achievement of strong contamination-free lamination operations. Post-fabrication filling of kerfs allow one to utilize transducer fabrication process steps such as curing and/or lamination steps or soldering steps whose processing temperatures are above those which would otherwise damage the kerf-filling material or redistribute it in an undesirable manner if it were present at that stage of fabrication. The application of the electrode closest the patient benefits in this manner. Cleaning associated with laminations is also simplified since the kerf-filling organic material is not introduced until later. A rigid permeable yet attenuative backing also allows one to pull a vacuum on the entire probe volume including kerfs 5 before potting or filling steps are executed in order to avoid introducing bubbles into the kerfs. It also allows for the better flow of dicing coolant around the elements during their cutting (dicing) definition.

Finally, these fused backings allow improved void-free adhesive joints to be made between the electrode surfaces 3 and backing 4 regardless of what form the electrode takes. This is both because epoxy air bubbles may escape into the backing and because of increased mechanical adhesive interlocking arising from the surface porosity of backing 4. Acoustically thin bondlines can be made to such permeable materials as long as only a thin film of epoxy or some direct fusing process is utilized between backing 4 and electrode 3.

In the case wherein the kerfs 5 are post-filled, as described above, each piezoelectric element 1 becomes mechanically anchored not only by its bond to directly underlying layer electrode 3 and backing 4 but also by its bonds to the kerf filler material which itself is bonded, indeed saturated, into the backing 4. The result, in the case of the kerfs being filled as by the introduction of filler material through the permeable paths of the backing material 4 of this invention, is that each element is extremely well anchored and potted in spatial position. The kerf material, being directly saturated into the backing 4, essentially eliminates any concern about the bondstrength of that material to backing 4. Post-filled kerfs also result in a somewhat more strongly laminated and tougher more rigid transducer (particularly in the direction 12) and one in which it is less likely that liquid agents used in fabrication or during application will be able to enter and cause corrosion. Stronger laminations in the direction 11 are possible because the organic filler material is not present even in trace contaminant amounts to hurt adhesive strength at the time of stack lamination operations.

Figure 3:
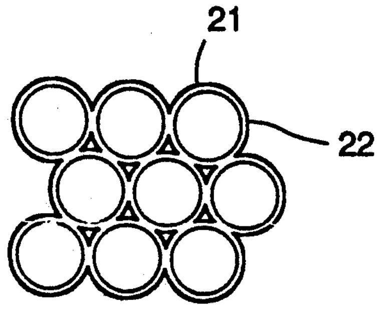
FIG. 3 is a cross-sectional view of a second embodiment of the backing structure employing polymer-coated particles fused into a macroscopically rigid backing structure.

A second embodiment of fused backing 4 shown in FIG. 3 consists of fused coated ceramic or metal particles 21 which have a higher impedance and a somewhat decreased attenuation compared to the fused polymeric particles of FIG. 2. For acoustic designs wherein one is trying to more closely match the impedance of the backing to that of the piezoelectric element array, as is frequently done with conventional tungsten-filled backers, this second embodiment can be utilized. The fused polymeric particle backings are all of a low impedance and may be used to purposely mismatch the backing 4 and piezoelectric element 1 acoustic impedances to minimize backing acoustic energy injection. Together the two embodiments of backing materials cover any acoustic design requirement calling for a low, intermediate or high backing impedance.

In this second embodiment, one may construct a backing 4 also using the PARYLENE CVD process described. This is possible by employing high impedance high density metallic particles such as tungsten and using the CVD process to both uniformly tumble the metallic particles and to subsequently bond them together in a separate PARYLENE particle-fusing operation. The metallic particles are precoated in a tumbler within the deposition chamber with the polymer conformal film 22 before they are compacted. In order to fuse the preciated particles together, one compacts them and utilizes any of the processes already described for fusing the first embodiment including thermal diffusion, thermal welding, solvent welding or acoustic welding. A parylene may be chosen which, itself, is thermally fusible or parylene may cause welding of said coated particles simply via deposition on the many internal contacting surfaces. Thus, there are minimal direct metal-to-metal interparticle contacts in the fused compacted structure. Because of this, acoustic waves must pass along tortuous paths of alternating metal and polymer thus providing substantial attenuation. Rigidity and thermal stability are provided by the stiff metal or ceramic particles and by the semirigid PARYLENE particle coatings and fusing impregnation (if used) and by the good thermal stability of the particles and any PARYLENE itself. The PARYLENE particle coating may be from a few thousand angstroms thick to tens of microns thick. The particle coating thickness determines final particle separation and therefore density and impedance. It will typically be of a thickness on the order of the particle diameter. The second (fusing) coating need only be of a thickness equal to a small fraction of the as-coated particle diameter. As a specific example, one might use 30 micron tungsten particles, an 8 micron thick particle coating and a two micron fusing PARYLENE impregnation. Such tungsten based backings have been constructed and fused using a temp/-pressure cycle on the precoated particles and a fusible parylene. An alternately available approach for this embodiment is to saturate the compacted particles with low viscosity epoxy. This, however, will sacrifice the later option of impregnating the kerfs.

With the low impedance polymeric-based particle backing 4 of the first embodiment, one insures that there is little acoustic energy coupled into the backing block from the piezoelectric elements. What little energy is coupled into the back is fully attenuated before it can reflect off the bottom of the backing and arrive back at the piezoelectric element to generate an undesirable electrical signal.

With the higher-impedance coated metallic or ceramic based particle backing of the second embodiment, one completes the toolset for being able to build virtually any conceivable transducer and gain all of the described benefits of this invention.

It has also been found that a highly desirable feature for those cases where transducer components 1,2,3 and 6 are to be patterned with a dicing saw and where certain of those layers extend to or near to the edges of the backing 4 of this invention one may advantageously utilize an auxiliary container or can 13. The container or can 13 typically is made of metal, such as copper with a nickel plating overcoat. The backing 4 is attached to the bottom of the can with a thin epoxy preform 17 or is formed in the can to begin with. The use of a preform insures that the pores of backing 4 are not filled by the attachment adhesive used for bonding backing 4 into can 13. An important benefit of such a full or partial can 13 is that it provides mechanical rigidity during dicing at the extreme edges of the diced layers at the regions wherein piezoelectric elements 1 and electrodes 2 and 3 meet the edges of backing 4. This prevents dicing edge damage. The metal container 13 also provides an electrical path, an RFI shielding function, a thermal heat-sinking path and a convenient fabrication carrier for backing 4. It may also act as a container to restrict or control the flow of potting or kerf-filling impregnation material which is introduced into backing 4 and/or into the kerfs 5, typically after stack construction.

For making the permeable backing 4, high-speed diamond-abrasive dicing in a coolant is an excellent way to serve the function of creating the edges 19 of the backing 4. In this manner these edges do not have to be formed when the permeable material is itself created. This allows one to make the material in larger sheet form. The permeability of the backing 4 permits superior coolant flow in and around the cutting action, resulting in edge 19 surfaces with minimal smear or thermal damage. This is not easily possible with alternative techniques such as laser machining or water-jet cutting. With those techniques one finds more surface damage, more macroscopic path distortion and more edge taper.

In summary, this invention provides an implementation method, structure and materials for a medical-ultrasound transducer 16 amenable to miniaturization, low in-process and in-use distortion, maximum physical strength, lightweight, the fabrication-postponement of kerf-filling processes which can hurt the adhesive strengths of laminations, the use of high-temperature transducer processing and the post-fabrication curvature of devices as for a curvilinear array.

We claim:

1. In an ultrasound transducer having at least one array of piezoelectric transducer elements separated by kerfs and top and bottom electrodes for individually addressing each transducer element of the at least one array, an improved backing upon which the transducer elements and electrodes are mounted comprising rigid polymeric or polymer-coated particles fused into a macroscopically rigid structure having remnant tortuous permeability to provide high acoustic attenuation and to permit fluid passage into the structure.

2. The ultrasound transducer of claim 1 wherein the remnant tortuous permeability of said backing has a median pore size in the range of 15–100 microns.

3. The ultrasound transducer of claim 1 wherein the backing has an acoustic attenuation of at least 3 dB/mm at 1 Mhz.

4. The ultrasound transducer of claim 1 wherein the polymeric particles have a glass transition temperature of at least 100° C.

5. The ultrasound transducer of claim 1 wherein the polymer coating of said polymer coated particles has a glass transition temperature of at least 50° C.

6. The ultrasound transducer of claim 1 wherein the polymeric particles are selected from a group of plastics consisting of polysulfone (PS), polyethersulfone (PES), polycarbonate (PC), polytetrafluoroethylene (PTFE), polyvinylidene fluoride (PVDF), ultrahigh density high molecular weight polyethylene (UDHMWPE), low and medium density polyethylene (PE), perfluoroalkoxy (PFA), fluorinated ethylene propylene (FEP), polytrifluorochloroethylene (CTFE), chlorotrifluoroethylene (CTFE, ECTFE), polyaryl sulfone, polyester and acrylonitrilebutadiene-styrene (ABS).

7. The ultrasound transducer of claim 1 wherein the polymer-coated particles are selected from the group consisting of coated high impedance metals, such as tungsten or any ceramic.

8. The ultrasound transducer of claim 1 wherein the polymer-coated particles are selected from the group consisting of coated high impedance metals, such as tungsten or any ceramic such as PZT or lead zirconate titanate.

9. The transducer of claim I further including kerfs filled with a lossy elastomeric or gel-like kerf-filling material permeated through the backing.

10. The transducer of claim 1 wherein the backing laminated to the piezoelectric transducer elements and their accompanying matching layer and electrodes is fabricated flat and then formed over a curved ceramic or metal mandrel.

11. The ultrasound transducer of claim 1 further comprising a metal container for improved rigidity, electrical shielding or heat transfer.

12. A method for fabricating an ultrasound transducer having at least one array of piezoelectric transducer elements separated by kerfs and top and bottom electrodes for individually addressing each transducer element of the at least one array comprising:

fusing polymer coated particles by applying elevated pressure and temperature to produce direct fusion between particles with an improved backing.

13. The method of claim 12 wherein the compacted particles are selected from the group of parylenes consisting of parylene N, parylene C, parylene D or parylene E.

14. A method for fabricating an ultrasound transducer having at least one array of piezoelectric transducer elements separated by kerfs and top and bottom electrodes for individually addressing each transducer element of the at least one array comprising:

fusing polymeric particles or polymeric coated particles by bringing them into close proximity to each other via compaction, then exposing the compacted particles to a gaseous polymeric thin film deposition to cause fusion with an improved backing.

15. The method of claim 14 wherein the compacted particles are selected from the group of parylenes consisting of parylene N, parylene C, parylene D or parylene E.

16. A method for fabricating an ultrasound transducer having at least one array of piezoelectric transducer elements separated by kerfs and top and bottom electrodes for individually addressing each transducer element of the at least one array comprising:

fusing polymer coated particles by bringing them into close proximity to each other via compaction, then saturating said compacted particles with an epoxy or castable low-viscosity polymer to cause fusion with an improved backing.

17. A method for fabricating an ultrasound transducer having at least one array of piezoelectric transducer elements separated by kerfs and top and bottom electrodes for individually addressing each transducer element of the at least one array comprising:

fusing polymeric particles or polymeric coated particles by bringing them into close proximity to each other via compaction, then welding the compacted particles with the aid of acoustic welding.

18. A method for fabricating an ultrasound transducer having at least one array of piezoelectric transducer elements separated by kerfs and top and bottom electrodes for individually addressing each transducer element of the at least one array comprising:

fusing polymeric particles or polymeric coated particles by bringing them into close proximity to each other via compaction, then welding the compacted particles with the aid of solvent.

* * * * *